United States Patent
Gesswein et al.

(10) Patent No.: US 8,029,530 B2
(45) Date of Patent: Oct. 4, 2011

(54) GUIDE WIRE WITH EMBOLIC FILTERING ATTACHMENT

(75) Inventors: Douglas H. Gesswein, Temecula, CA (US); Wayne E. Cornish, Fallbrook, CA (US); Scott J. Huter, Temecula, CA (US); Benjamin C. Huter, Murrieta, CA (US); John E. Papp, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 12/904,001

(22) Filed: Oct. 13, 2010

(65) Prior Publication Data

US 2011/0029008 A1    Feb. 3, 2011

Related U.S. Application Data

(60) Division of application No. 12/025,404, filed on Feb. 4, 2008, now Pat. No. 7,815,660, which is a continuation of application No. 10/260,718, filed on Sep. 30, 2002, now Pat. No. 7,331,973.

(51) Int. Cl.
*A61F 2/01* (2006.01)
(52) U.S. Cl. .................................... 606/200
(58) Field of Classification Search .............. 606/200, 606/110, 113, 114, 127, 108, 198, 159, 126, 606/194–197; 604/164.03; 600/585; 128/898
See application file for complete search history.

(56) References Cited

U.S. PATENT DOCUMENTS

| | | |
|---|---|---|
| 3,952,747 A | 4/1976 | Kimmell, Jr. |
| 4,425,908 A | 1/1984 | Simon |

(Continued)

FOREIGN PATENT DOCUMENTS

EP     0427429 A3    9/1991

(Continued)

OTHER PUBLICATIONS

Dilitation of the Carotid Artery by a Temporary Carotid Filter by A. Beck, St. Milic, A.M. Spagnoli, November-December Issue of OPLITAI, An International Journal on Military Medicine and Health Emergencies, pp. 67-74.

(Continued)

*Primary Examiner* — Elizabeth Houston
(74) *Attorney, Agent, or Firm* — Fulwider Patton LLP; Abbott Vascular; Jonathan Feuchtwang (57) ABSTRACT

A separate deliverable embolic protection device filter that attaches to a helical coil at a distal end of a conventional guide, for use in a blood vessel when an interventional procedure is being performed to capture any embolic material which may be created and released into the bloodstream during the procedure. The device includes a filter assembly with a proximal end and a distal end, and a guide wire connector attached to the distal end of the filter assembly. The guide wire connector is able to couple with the helical coil of the guide wire. A restraining sheath placed over the filter assembly in a coaxial arrangement maintains the filter assembly in a collapsed position and delivers the filter assembly separately to the helical coil of the guide wire, and then the guide wire connector is joined to the helical coil. Alternatively, the guide wire can include a rotatable coil section forming a portion of the distal tip coil on the guide wire which is adapted to be coupled to the filter assembly. This arrangement allows the filter assembly to be rotatably mounted onto the guide wire.

19 Claims, 7 Drawing Sheets

U.S. PATENT DOCUMENTS

| | | |
|---|---|---|
| 4,494,531 A | 1/1985 | Gianturco |
| 4,612,931 A | 9/1986 | Dormia |
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,154,705 A * | 10/1992 | Fleischhacker et al. ...... 604/526 |
| 5,158,548 A | 10/1992 | Lau |
| 5,160,342 A | 11/1992 | Reger et al. |
| 5,192,286 A | 3/1993 | Phan et al. |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A * | 2/1996 | Mische et al. ................ 606/159 |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,613,981 A | 3/1997 | Boyle et al. |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,662,703 A | 9/1997 | Yurek et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,214,040 B1 | 4/2001 | Jayaraman |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,119 B1 | 6/2001 | Addis |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaosian |
| 6,270,513 B1 | 8/2001 | Tsugita et al. |
| 6,273,901 B1 | 8/2001 | Whitcher et al. |
| 6,277,138 B1 * | 8/2001 | Levinson et al. ............. 606/200 |

| Patent No. | Date | Name |
|---|---|---|
| 6,277,139 B1 | 8/2001 | Levinson et al. |
| 6,280,451 B1 | 8/2001 | Bates et al. |
| 6,287,321 B1 | 9/2001 | Jang |
| 6,290,656 B1 | 9/2001 | Boyle et al. |
| 6,290,710 B1 | 9/2001 | Cryer et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 | 1/2002 | Gilson et al. |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,364,900 B1 | 4/2002 | Heuser |
| 6,371,969 B1 | 4/2002 | Tsugita et al. |
| 6,371,970 B1 | 4/2002 | Khosravi et al. |
| 6,371,971 B1 * | 4/2002 | Tsugita et al. ............ 606/200 |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Peterson |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,768 B1 | 4/2003 | Diaz et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 | 7/2003 | Huter et al. |
| 6,599,308 B2 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,635,070 B2 | 10/2003 | Leeflang et al. |
| 6,638,293 B1 | 10/2003 | Makowner et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 | 12/2003 | Papp et al. |
| 6,656,203 B2 | 12/2003 | Roth et al. |
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,673,090 B2 | 1/2004 | Root et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |

| Patent No. | Date | Inventor(s) |
|---|---|---|
| 6,695,864 B2 | 2/2004 | Macoviak et al. |
| 6,696,666 B2 | 2/2004 | Weber et al. |
| 6,699,260 B2 | 3/2004 | Dubrul et al. |
| 6,702,834 B1 | 3/2004 | Boylan et al. |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 * | 8/2004 | Kusleika et al. .............. 606/200 |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha et al. |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salaheih et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogenkijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Petersen |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B1 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,094,249 B1 * | 8/2006 | Broome et al. ................ 606/200 |
| 2002/0156456 A1 | 10/2002 | Fisher |
| 2002/0156457 A1 | 10/2002 | Fisher |
| 2002/0161390 A1 | 10/2002 | Mouw |
| 2002/0161392 A1 | 10/2002 | Dubrul |
| 2002/0161393 A1 | 10/2002 | Demond et al. |
| 2002/0161395 A1 | 10/2002 | Douk et al. |
| 2002/0165576 A1 | 11/2002 | Boyle et al. |
| 2002/0169414 A1 | 11/2002 | Kletschka |
| 2002/0169458 A1 | 11/2002 | Connors, III |
| 2002/0169472 A1 | 11/2002 | Douk et al. |
| 2002/0169474 A1 | 11/2002 | Kusleika et al. |
| 2002/0173815 A1 | 11/2002 | Hogendijk et al. |
| 2002/0173817 A1 | 11/2002 | Kletschka et al. |
| 2002/0188313 A1 | 12/2002 | Johnson et al. |
| 2002/0188314 A1 | 12/2002 | Anderson et al. |
| 2002/0193825 A1 | 12/2002 | McGuckin et al. |
| 2002/0193826 A1 | 12/2002 | McGuckin et al. |
| 2002/0193827 A1 | 12/2002 | McGuckin et al. |
| 2002/0193828 A1 | 12/2002 | Griffin et al. |
| 2003/0004536 A1 | 1/2003 | Boylan et al. |
| 2003/0004537 A1 | 1/2003 | Boyle et al. |
| 2003/0004539 A1 | 1/2003 | Linder et al. |
| 2003/0004540 A1 | 1/2003 | Linder et al. |
| 2003/0004541 A1 | 1/2003 | Linder et al. |
| 2003/0009188 A1 | 1/2003 | Linder et al. |
| 2003/0009189 A1 | 1/2003 | Gilson et al. |
| 2003/0015206 A1 | 1/2003 | Roth et al. |
| 2003/0018354 A1 | 1/2003 | Roth et al. |
| 2003/0023265 A1 | 1/2003 | Forber |
| 2003/0028238 A1 | 2/2003 | Burkett et al. |
| 2003/0032941 A1 | 2/2003 | Boyle et al. |
| 2003/0032977 A1 | 2/2003 | Brady et al. |
| 2003/0040772 A1 | 2/2003 | Hyodoh et al. |
| 2003/0042186 A1 | 3/2003 | Boyle et al. |
| 2003/0045898 A1 | 3/2003 | Harrison et al. |
| 2003/0057156 A1 | 3/2003 | Peterson et al. |
| 2003/0060782 A1 | 3/2003 | Bose et al. |
| 2003/0060843 A1 | 3/2003 | Boucher |
| 2003/0060844 A1 | 3/2003 | Borillo et al. |
| 2003/0065354 A1 | 4/2003 | Boyle et al. |
| 2003/0069596 A1 | 4/2003 | Eskuri |
| 2003/0069597 A1 | 4/2003 | Petersen |
| 2003/0078519 A1 | 4/2003 | Salahieh et al. |
| 2003/0078614 A1 | 4/2003 | Satahieh et al. |
| 2003/0083692 A1 | 5/2003 | Vrba et al. |
| 2003/0083693 A1 | 5/2003 | Daniel et al. |
| 2003/0097095 A1 | 5/2003 | Brady et al. |
| 2003/0100917 A1 | 5/2003 | Boyle et al. |
| 2003/0100918 A1 | 5/2003 | Duane |

| | | | | | |
|---|---|---|---|---|---|
| 2003/0105484 A1 | 6/2003 | Boyle et al. | 2004/0088000 A1 | 5/2004 | Muller |
| 2003/0109824 A1 | 6/2003 | Anderson et al. | 2004/0088002 A1 | 5/2004 | Boyle et al. |
| 2003/0114879 A1 | 6/2003 | Euteneuer et al. | 2004/0093009 A1 | 5/2004 | Denison et al. |
| 2003/0114880 A1 | 6/2003 | Hansen et al. | 2004/0093010 A1 | 5/2004 | Gesswein et al. |
| 2003/0120303 A1 | 6/2003 | Boyle et al. | 2004/0093011 A1 | 5/2004 | Vrba |
| 2003/0125764 A1 | 7/2003 | Brady et al. | 2004/0093012 A1 | 5/2004 | Cully et al. |
| 2003/0130680 A1 | 7/2003 | Russell | 2004/0093013 A1 | 5/2004 | Brady et al. |
| 2003/0130681 A1 | 7/2003 | Ungs | 2004/0098022 A1 | 5/2004 | Barone |
| 2003/0130682 A1 | 7/2003 | Broome et al. | 2004/0098026 A1 | 5/2004 | Joergensen et al. |
| 2003/0130684 A1 | 7/2003 | Brady et al. | 2004/0098032 A1 | 5/2004 | Papp et al. |
| 2003/0130685 A1 | 7/2003 | Daniel et al. | 2004/0098033 A1 | 5/2004 | Leeflang et al. |
| 2003/0130686 A1 | 7/2003 | Daniel et al. | 2004/0102807 A1 | 5/2004 | Kusleika et al. |
| 2003/0130687 A1 | 7/2003 | Daniel et al. | 2004/0106944 A1 | 6/2004 | Daniel et al. |
| 2003/0130688 A1 | 7/2003 | Daniel et al. | 2004/0111111 A1 | 6/2004 | Lin |
| 2003/0135162 A1 | 7/2003 | Deyette, Jr. et al. | 2004/0116960 A1 | 6/2004 | Demond et al. |
| 2003/0135232 A1 | 7/2003 | Douk et al. | 2004/0122466 A1 | 6/2004 | Bales |
| 2003/0139764 A1 | 7/2003 | Levinson et al. | 2004/0127933 A1 | 7/2004 | Demond et al. |
| 2003/0144685 A1 | 7/2003 | Boyle et al. | 2004/0127934 A1 | 7/2004 | Gilson et al. |
| 2003/0144689 A1 | 7/2003 | Brady et al. | 2004/0127936 A1 | 7/2004 | Salaheih et al. |
| 2003/0150821 A1 | 8/2003 | Bates et al. | 2004/0138693 A1 | 7/2004 | Eskuri et al. |
| 2003/0153935 A1 | 8/2003 | Mialhe | 2004/0138694 A1 | 7/2004 | Tran et al. |
| 2003/0153943 A1 | 8/2003 | Michael et al. | 2004/0138696 A1 | 7/2004 | Drasler et al. |
| 2003/0158574 A1 | 8/2003 | Esch et al. | 2004/0147955 A1 | 7/2004 | Beulke et al. |
| 2003/0163064 A1 | 8/2003 | Vrba et al. | 2004/0153118 A1 | 8/2004 | Clubb et al. |
| 2003/0171770 A1 | 9/2003 | Anderson et al. | 2004/0153119 A1 | 8/2004 | Kusleika et al. |
| 2003/0171771 A1 | 9/2003 | Anderson | 2004/0158275 A1 | 8/2004 | Crank et al. |
| 2003/0176884 A1 | 9/2003 | Berrada et al. | 2004/0158277 A1 | 8/2004 | Lowe et al. |
| 2003/0176885 A1 | 9/2003 | Broome et al. | 2004/0158278 A1 | 8/2004 | Becker et al. |
| 2003/0176886 A1 | 9/2003 | Wholey et al. | 2004/0158279 A1 | 8/2004 | Petersen |
| 2003/0176889 A1 | 9/2003 | Boyle et al. | 2004/0158280 A1 | 8/2004 | Morris et al. |
| 2003/0181943 A1 | 9/2003 | Daniel et al. | 2004/0158281 A1 | 8/2004 | Boylan et al. |
| 2003/0187474 A1 | 10/2003 | Keegan et al. | 2004/0167564 A1 | 8/2004 | Fedie |
| 2003/0187475 A1 | 10/2003 | Tsugita et al. | 2004/0167565 A1 | 8/2004 | Beulke et al. |
| 2003/0187495 A1 | 10/2003 | Cully et al. | 2004/0167566 A1 | 8/2004 | Beulke et al. |
| 2003/0191493 A1 | 10/2003 | Epstein et al. | 2004/0167567 A1 | 8/2004 | Cano et al. |
| 2003/0195554 A1 | 10/2003 | Shen et al. | 2004/0167568 A1 | 8/2004 | Boyle et al. |
| 2003/0195555 A1 | 10/2003 | Khairkhahan et al. | 2004/0172055 A1 | 9/2004 | Huter et al. |
| 2003/0195556 A1 | 10/2003 | Stack et al. | 2004/0176794 A1 | 9/2004 | Khosravi |
| 2003/0199819 A1 | 10/2003 | Beck | 2004/0193208 A1 | 9/2004 | Talpade et al. |
| 2003/0199921 A1 | 10/2003 | Palmer et al. | 2004/0199198 A1 | 10/2004 | Beulke et al. |
| 2003/0204168 A1 | 10/2003 | Bosme et al. | 2004/0199199 A1 | 10/2004 | Krolik et al. |
| 2003/0204202 A1 | 10/2003 | Palmer et al. | 2004/0199203 A1 | 10/2004 | Oslund et al. |
| 2003/0208222 A1 | 11/2003 | Zadno-Azizi | 2004/0204737 A1 | 10/2004 | Boismier et al. |
| 2003/0208224 A1 | 11/2003 | Broome | 2004/0210250 A1 | 10/2004 | Eskuri |
| 2003/0208225 A1 | 11/2003 | Goll et al. | 2004/0215230 A1* | 10/2004 | Frazier et al. .................. 606/200 |
| 2003/0208226 A1 | 11/2003 | Bruckheimer et al. | 2004/0220608 A1 | 11/2004 | D'Aquanni et al. |
| 2003/0208227 A1 | 11/2003 | Thomas | 2004/0220609 A1 | 11/2004 | Douk et al. |
| 2003/0208228 A1 | 11/2003 | Gilson et al. | 2004/0220611 A1 | 11/2004 | Ogle |
| 2003/0208229 A1 | 11/2003 | Kletschka | 2004/0225322 A1 | 11/2004 | Garrison et al. |
| 2003/0212361 A1 | 11/2003 | Boyle et al. | 2004/0236368 A1 | 11/2004 | McGucklin, Jr. et al. |
| 2003/0212429 A1 | 11/2003 | Keegan et al. | 2004/0236369 A1 | 11/2004 | Dubrul |
| 2003/0212431 A1 | 11/2003 | Brady et al. | 2004/0249409 A1 | 12/2004 | Krolik et al. |
| 2003/0212434 A1 | 11/2003 | Thielen | 2004/0254601 A1 | 12/2004 | Eskuri |
| 2003/0216774 A1 | 11/2003 | Larson | 2004/0254602 A1 | 12/2004 | Lehe et al. |
| 2003/0220665 A1 | 11/2003 | Eskuri et al. | 2004/0260308 A1 | 12/2004 | Gilson et al. |
| 2003/0225418 A1 | 12/2003 | Eskuri et al. | 2004/0260333 A1 | 12/2004 | Dubrul et al. |
| 2003/0225435 A1 | 12/2003 | Huter et al. | 2004/0267301 A1 | 12/2004 | Boylan et al. |
| 2003/0229295 A1 | 12/2003 | Houde et al. | 2004/0267302 A1 | 12/2004 | Gilson et al. |
| 2003/0229374 A1 | 12/2003 | Brady et al. | 2005/0004594 A1 | 1/2005 | Nool et al. |
| 2003/0233117 A1 | 12/2003 | Adams et al. | 2005/0004595 A1 | 1/2005 | Boyle et al. |
| 2003/0236545 A1 | 12/2003 | Gilson | 2005/0004597 A1 | 1/2005 | McGuckin, Jr. et al. |
| 2004/0002730 A1 | 1/2004 | Denison et al. | 2005/0010245 A1 | 1/2005 | Wasicek |
| 2004/0006361 A1 | 1/2004 | Boyle et al. | 2005/0010246 A1 | 1/2005 | Streeter et al. |
| 2004/0006364 A1 | 1/2004 | Ladd | 2005/0010247 A1 | 1/2005 | Kusleika et al. |
| 2004/0006365 A1 | 1/2004 | Brady et al. | 2005/0021075 A1 | 1/2005 | Bonnette et al. |
| 2004/0006366 A1 | 1/2004 | Huter et al. | 2005/0021076 A1 | 1/2005 | Mazzocchi et al. |
| 2004/0006367 A1 | 1/2004 | Johnson et al. | 2005/0055048 A1 | 3/2005 | Dieck et al. |
| 2004/0006368 A1 | 1/2004 | Mazzocchi et al. | 2005/0070953 A1 | 3/2005 | Riley |
| 2004/0015184 A1 | 1/2004 | Boyle et al. | 2005/0075663 A1 | 4/2005 | Boyle et al. |
| 2004/0019363 A1 | 1/2004 | Hanson et al. | 2005/0080446 A1 | 4/2005 | Gilson et al. |
| 2004/0034385 A1 | 2/2004 | Gilson et al. | 2005/0085842 A1 | 4/2005 | Eversull et al. |
| 2004/0039411 A1 | 2/2004 | Gilson et al. | 2005/0090845 A1 | 4/2005 | Boyd |
| 2004/0044359 A1 | 3/2004 | Renati et al. | 2005/0090857 A1 | 4/2005 | Kusleika et al. |
| 2004/0044360 A1 | 3/2004 | Lowe | 2005/0090858 A1 | 4/2005 | Pavlovic |
| 2004/0049226 A1 | 3/2004 | Keegan et al. | 2005/0096691 A1 | 5/2005 | Groothuis et al. |
| 2004/0059372 A1 | 3/2004 | Tsugita | 2005/0096692 A1 | 5/2005 | Linder et al. |
| 2004/0059373 A1 | 3/2004 | Shapiro et al. | 2005/0101986 A1 | 5/2005 | Daniel et al. |
| 2004/0082697 A1 | 4/2004 | Broome et al. | 2005/0101987 A1 | 5/2005 | Salahich |
| 2004/0082968 A1 | 4/2004 | Krolik et al. | 2005/0101988 A1 | 5/2005 | Stanford et al. |

| Publication No. | Date | Inventors |
|---|---|---|
| 2005/0101989 A1 | 5/2005 | Cully et al. |
| 2005/0113865 A1 | 5/2005 | Daniel et al. |
| 2005/0119688 A1 | 6/2005 | Bergheim |
| 2005/0119689 A1 | 6/2005 | Mazzocchi et al. |
| 2005/0119690 A1 | 6/2005 | Mazzocchi et al. |
| 2005/0119691 A1 | 6/2005 | Daniel et al. |
| 2005/0124931 A1 | 6/2005 | Fulton et al. |
| 2005/0125023 A1 | 6/2005 | Bates et al. |
| 2005/0131450 A1 | 6/2005 | Nicholson et al. |
| 2005/0131453 A1 | 6/2005 | Parodi |
| 2005/0149110 A1 | 7/2005 | Wholey et al. |
| 2005/0149112 A1 | 7/2005 | Barbut |
| 2005/0149113 A1 | 7/2005 | Douk et al. |
| 2005/0159772 A1 | 7/2005 | Lowe et al. |
| 2005/0159773 A1 | 7/2005 | Broome et al. |
| 2005/0159774 A1 | 7/2005 | Belef |
| 2005/0171573 A1 | 8/2005 | Salahieh et al. |
| 2005/0177187 A1 | 8/2005 | Gray et al. |
| 2005/0182440 A1 | 8/2005 | Bates et al. |
| 2005/0182441 A1 | 8/2005 | Denison et al. |
| 2005/0192623 A1 | 9/2005 | Mazzocchi et al. |
| 2005/0192624 A1 | 9/2005 | Mazzocchi et al. |
| 2005/0203567 A1 | 9/2005 | Linder et al. |
| 2005/0203568 A1 | 9/2005 | Burg et al. |
| 2005/0203569 A1 | 9/2005 | Kusleika et al. |
| 2005/0203570 A1 | 9/2005 | Mazzocchi et al. |
| 2005/0203571 A1 | 9/2005 | Mazzocchi et al. |
| 2005/0209634 A1 | 9/2005 | Brady et al. |
| 2005/0209635 A1 | 9/2005 | Gilson et al. |
| 2005/0216051 A1 | 9/2005 | Mazzocchi et al. |
| 2005/0216052 A1 | 9/2005 | Mazzocchi et al. |
| 2005/0216053 A1 | 9/2005 | Douk et al. |
| 2005/0222583 A1 | 10/2005 | Cano et al. |
| 2005/0222604 A1 | 10/2005 | Schaeffer et al. |
| 2005/0222607 A1 | 10/2005 | Palmer et al. |
| 2005/0228437 A1 | 10/2005 | Gilson et al. |
| 2005/0228438 A1 | 10/2005 | Sachar et al. |
| 2005/0228439 A1 | 10/2005 | Andrews et al. |
| 2005/0234502 A1 | 10/2005 | Gilson et al. |
| 2005/0240215 A1 | 10/2005 | Ellis |
| 2005/0245866 A1 | 11/2005 | Azizi |
| 2005/0267517 A1 | 12/2005 | Ungs |
| 2005/0283184 A1 | 12/2005 | Gilson et al. |
| 2005/0283185 A1 | 12/2005 | Linder et al. |
| 2005/0283186 A1 | 12/2005 | Berrada et al. |
| 2005/0288705 A1 | 12/2005 | Gilson et al. |
| 2006/0004403 A1 | 1/2006 | Gilson et al. |
| 2006/0004405 A1 | 1/2006 | Salaheih et al. |
| 2006/0015138 A1 | 1/2006 | Gertner et al. |
| 2006/0015139 A1 | 1/2006 | Tsugita et al. |
| 2006/0015141 A1 | 1/2006 | Linder et al. |
| 2006/0020285 A1 | 1/2006 | Niermann |
| 2006/0020286 A1 | 1/2006 | Niermann |
| 2006/0025803 A1 | 2/2006 | Mitelberg et al. |
| 2006/0025804 A1 | 2/2006 | Krolik et al. |
| 2006/0025805 A1 | 2/2006 | DoBrava et al. |
| 2006/0030876 A1 | 2/2006 | Peacock, III et al. |
| 2006/0030877 A1 | 2/2006 | Martinez et al. |
| 2006/0030878 A1 | 2/2006 | Anderson et al. |
| 2006/0052817 A1 | 3/2006 | Russo et al. |
| 2006/0074446 A1 | 4/2006 | Gilson et al. |
| 2006/0095069 A1 | 5/2006 | Shah et al. |
| 2006/0100659 A1 | 5/2006 | Dinh et al. |
| 2006/0100662 A1 | 5/2006 | Daniel et al. |
| 2006/0100663 A1 | 5/2006 | Palmer et al. |
| 2006/0116715 A1 | 6/2006 | Khosravi et al. |
| 2006/0122643 A1 | 6/2006 | Wasicek |
| 2006/0122644 A1 | 6/2006 | Brady et al. |
| 2006/0122645 A1 | 6/2006 | Brady et al. |
| 2006/0129181 A1 | 6/2006 | Callol et al. |
| 2006/0129182 A1 | 6/2006 | Gilson et al. |
| 2006/0129183 A1 | 6/2006 | Boyle et al. |
| 2006/0149312 A1 | 7/2006 | Arguello et al. |
| 2006/0149313 A1 | 7/2006 | Arguello et al. |
| 2006/0149314 A1 | 7/2006 | Borillo et al. |
| 2006/0155322 A1 | 7/2006 | Sater et al. |
| 2006/0161198 A1 | 7/2006 | Sakai et al. |
| 2006/0167491 A1 | 7/2006 | Wholey et al. |
| 2006/0184194 A1 | 8/2006 | Pal et al. |
| 2006/0190025 A1 | 8/2006 | Lehe et al. |
| 2006/0195137 A1 | 8/2006 | Sepetka et al. |
| 2006/0195138 A1 | 8/2006 | Goll et al. |
| 2006/0200047 A1 | 9/2006 | Galdonik et al. |
| 2006/0200191 A1 | 9/2006 | Zadno-Azizi |
| 2006/0206139 A1 | 9/2006 | Tekulve |

FOREIGN PATENT DOCUMENTS

| | | |
|---|---|---|
| EP | 0472334 A1 | 2/1992 |
| EP | 0533511 A1 | 3/1993 |
| EP | 1 127 556 A2 | 8/2001 |
| EP | 1 127 556 A3 | 8/2001 |
| FR | 2580504 A1 | 10/1986 |
| GB | 2020557 | 11/1979 |
| WO | WO92/03097 | 3/1992 |
| WO | WO96/01591 | 1/1996 |
| WO | WO97/17100 | 5/1997 |
| WO | WO98/02084 | 1/1998 |
| WO | WO98/33443 | 8/1998 |
| WO | WO99/16382 | 4/1999 |
| WO | WO99/22673 | 5/1999 |
| WO | WO 99/22673 * | 5/1999 |
| WO | WO99/23976 | 5/1999 |
| WO | WO99/44510 | 9/1999 |
| WO | WO00/67667 | 11/2000 |
| WO | WO01/10346 | 2/2001 |
| WO | WO01/12082 | 2/2001 |
| WO | WO01/45592 | 6/2001 |
| WO | WO01/87183 | 11/2001 |
| WO | WO02/28292 | 4/2002 |
| WO | WO2004/021928 | 3/2004 |

OTHER PUBLICATIONS

Minibasket for Percutaneous Embolectomy and Filter Protection Against Distal Embolization: Technical Note.

* cited by examiner

GUIDE WIRE WITH EMBOLIC FILTERING ATTACHMENT

CROSS-REFERENCE TO RELATED APPLICATIONS

This is a divisional of U.S. Ser. No. 12/025,404, filed Feb. 4, 2008 which is a continuation of U.S. Ser. No. 10/260,718, filed Sep. 30, 2002, U.S. Pat. No. 7,331,973, issued Feb. 19, 2008.

BACKGROUND OF THE INVENTION

The present invention relates generally to filtering devices used, for example, when an interventional procedure is being performed in a stenosed or occluded region of a body vessel to capture embolic material that may be created and released into the vessel during the procedure. The present invention is more particularly directed to a separately deliverable embolic filter assembly having an expandable basket and filter that can be attached to the distal tip coil of a conventional guide wire via a guide wire connector.

Numerous procedures have been developed for treating occluded blood vessels to allow blood to flow without obstruction. Such procedures usually involve the percutaneous introduction of an interventional device into the lumen of the artery, usually by a catheter. One widely known and medically accepted procedure is balloon angioplasty in which an inflatable balloon is introduced within the stenosed region of the blood vessel to dilate the occluded vessel. The balloon dilatation catheter is initially inserted into the patient's arterial system and is advanced and manipulated into the area of stenosis in the artery. The balloon is inflated to compress the plaque and press the vessel wall radially outward to increase the diameter of the blood vessel, resulting in increased blood flow. The balloon is then deflated to a small profile so that the dilatation catheter can be withdrawn from the patient's vasculature and the blood flow resumed through the dilated artery. As should be appreciated by those skilled in the art, while the above-described procedure is typical, it is not the only method used in angioplasty.

Another procedure is laser angioplasty which utilizes a laser to ablate the stenosis by super heating and vaporizing the deposited plaque. Atherectomy is yet another method of treating a stenosed body vessel in which cutting blades are rotated to shave the deposited plaque from the arterial wall. A vacuum catheter is usually used to capture the shaved plaque or thrombus from the blood stream during this procedure.

In the procedures of the kind referenced above, abrupt reclosure may occur or restenosis of the artery may develop over time, which may require another angioplasty procedure, a surgical bypass operation, or some other method of repairing or strengthening the area. To reduce the likelihood of the occurrence of reclosure and to strengthen the area, a physician can implant an intravascular prosthesis for maintaining vascular patency, commonly known as a stent, inside the artery across the lesion. The stent can be crimped tightly onto the balloon portion of the catheter and transported in its delivery diameter through the patient's vasculature. At the deployment site, the stent is expanded to a larger diameter, often by inflating the balloon portion of the catheter.

The above non-surgical interventional procedures, when successful, avoid the necessity of major surgical operations. However, there is one common problem which can become associated with all of these non-surgical procedures, namely, the potential release of embolic debris into the bloodstream that can occlude distal vasculature and cause significant health problems to the patient. For example, during deployment of a stent, it is possible that the metal struts of the stent can cut into the stenosis and create particles of plaque that can travel downstream and lodge somewhere in the patient's vascular system. Pieces of plaque material are sometimes generated during a balloon angioplasty procedure and are released into the bloodstream. Additionally, while complete vaporization of plaque is the intended goal during laser angioplasty, sometimes particles are not fully vaporized and enter the bloodstream. Likewise, not all of the emboli created during an atherectomy procedure may be drawn into the vacuum catheter and, as a result, may enter the bloodstream as well.

When any of the above-described procedures are performed in the carotid arteries, the release of emboli into the circulatory system can be extremely dangerous and sometimes fatal to the patient. Debris carried by the bloodstream to distal vessels of the brain can cause cerebral vessels to occlude, resulting in a stroke, and in some cases, death. Therefore, although cerebral percutaneous transluminal angioplasty has been performed in the past, the number of procedures performed has been somewhat limited due to the justifiable fear of an embolic stroke occurring should embolic debris enter the bloodstream and block vital downstream blood passages.

Medical devices have been developed to attempt to deal with the problem created when debris or fragments enter the circulatory system following vessel treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such a procedure in the carotid arteries a high-risk proposition.

Other techniques include the use of catheters with a vacuum source which provides temporary suction to remove embolic debris from the bloodstream. However, as mentioned above, there can be complications associated with such systems if the catheter does not remove all of the embolic material from the bloodstream. Also, a powerful suction could cause trauma to the patient's vasculature.

Another technique which has had some success utilizes a filter or trap downstream from the treatment site to capture embolic debris before it reaches the smaller blood vessels downstream. The placement of a filter in the patient's vasculature during treatment of the vascular lesion can reduce the presence of the embolic debris in the bloodstream. Such embolic filters are usually delivered in a collapsed position through the patient's vasculature and then expanded to trap the embolic debris. Some of these embolic filters are self expanding and utilize a restraining sheath which maintains the expandable filter in a collapsed position until it is ready to be expanded within the patient's vasculature. The physician can retract the proximal end of the restraining sheath to expose the expandable filter, causing the filter to expand at the desired location. Once the procedure is completed, the filter can be collapsed, and the filter (with the trapped embolic debris) can then be removed from the vessel. While a filter can be effective in capturing embolic material, the filter still needs to be collapsed and removed from the vessel. During this step, there is a possibility that trapped embolic debris can backflow through the inlet opening of the filter and enter the bloodstream as the filtering system is being collapsed and removed from the patient. Therefore, it is important that any captured embolic debris remain trapped within this filter so that particles are not released back into the body vessel.

Some prior art expandable filters vessel are attached to the distal end of a guide wire or guide wire-like member which allows the filtering device to be steered in the patient's vasculature as the guide wire is positioned by the physician. Once the guide wire is in proper position in the vasculature, the embolic filter can be deployed to capture embolic debris. The guide wire can then be used by the physician to deliver interventional devices, such as a balloon angioplasty dilatation catheter or a stent delivery catheter, to perform the interventional procedure in the area of treatment. After the procedure is completed, a recovery sheath can be delivered over the guide wire using over-the-wire or rapid exchange (RX) techniques to collapse the expanded filter for removal from the patient's vasculature.

Some prior art filtering devices utilize a construction in which the expandable filter is permanently affixed to the guide wire. When the expandable filter is permanently attached to the guide wire, the device may have added stiffness and therefore may lose some "front-line" capability, which is the ability to negotiate the often tortuous anatomy through which it is being delivered. The stiffness of a combined expandable filter and guide wire may possibly prevent the device from reaching the desired target area within the patient's vasculature. Also, in such a design, it is possible for the deployed filtering portion of the device to rotate or move with the guide wire in the event that the guide wire is rotated by the physician during usage. As a result, there is a possibility that the deployed filtering portion of the device could scrape the vessel wall possibly causing trauma. Therefore, when such a filtering device is utilized, it is important that the proximal end of the guide wire remains fixed since rotation could possible be transmitted to the deployed filtering portion of the device. However, since a physician normally delivers interventional devices along the guide wire after the filter portion has been deployed, some manipulation of the guide wire takes place an it may be difficult to prevent at least some rotation at the proximal end of the guide wire.

Some prior art filtering devices utilize a separate filtering assembly which can be delivered over the guide wire and attaches to a special fitting located near the distal end of the guide wire. However, these filtration devices require the fitting to be placed near the distal end of the guide wire which can possibly hinder the ability to steer the guide wire and reach the target area in the patient's vasculature. These particular filter systems also require additional manufacturing procedures to properly mount the fitting onto the steerable guide wire. As such, the presence of the fitting near the distal end of the guide wire may cause unwanted problems during delivery of the guide wire through the patient's vasculature.

Therefore, what has been needed is a filtering device that can be attached to the distal end of a guide wire after the guide wire has been initially deployed into the target region of a patient. The filter portion of the device should be easy to deliver, easily attachable to the guide wire and should eliminate the need for special fittings to be placed on the guide wire. Also, it would be beneficial if the filtering portion is rotatably mounted onto the guide wire to prevent the deployed filtering portion from rotating and possible scraping the vessel wall once deployed. The present invention satisfies these and other needs.

SUMMARY OF THE INVENTION

The present invention provides a separately deliverable filter assembly having an expandable basket (also referred to as a "cage") and a filter element that can be attached to the distal coil tip of a conventional guide wire. In use, the present invention is designed to capture embolic debris created during the performance of a therapeutic interventional procedure, such as a balloon angioplasty or stenting procedure, or other unwanted particulates entrained in the fluid of a body vessel. The present invention allows the physician to deliver the guide wire with "front-line" capabilities to steer through the tortuous anatomy, while still being able to provide filtering protection in the form of a separately deliverable attachment.

An embolic filtering device made in accordance with the present invention utilizes a filter assembly having an expandable basket capable of being disposed for traveling over the guide wire. The filter assembly has a proximal end and a distal end with a guide wire connector coupled to the distal end. Once in proper position, the guide wire connector is able to be coupled to the distal tip coil of the guide wire. The expandable basket can be made from a self-expanding material, for example, nickel-titanium alloy (NiTi), and may include struts capable of expanding from a collapsed position or configuration having a first delivery diameter to an expanded or deployed position or configuration having a second implanted diameter. The filter element may be made from an embolic-capturing material and is attached to the expandable basket such that it moves with the basket between the collapsed and deployed positions. Guide wire connectors of the present invention are easily adapted for attachment on a number of different configurations of filter assemblies and can be attached to a variety of different guide wires.

The guide wire used in the present invention may include steerable guide wires having distal tip coils which allow the guide wire connector to be screwed onto the tip coil. Also, any guide wire with coil spacing large enough to allow a guide wire connector having spring-loaded tabs to engage the tip coils may be implemented. Another guide wire that may be used in the present invention is found in U.S. Pat. No. 6,132,389 issued to Cornish et al., which discloses a proximally tapered guide wire tip coil. One embodiment of the present invention uses a variation of the coil tip design found in Cornish et al. patent, where the proximally tapered guide wire tip coil is stretched somewhat to create a matching coil to which the guide wire connector is attached.

In one particular embodiment of the present invention, the guide wire connector associated with the filter assembly is a connection coil capable of being screwed onto the helical coil of the guide wire. When a guide wire with a proximally tapered distal tip coil is used, the connection coil may have a similar pitch to the tip coil on the guide wire.

In another embodiment of the present invention, the guide wire connector associated with the filter assembly includes at least one spring-loaded tab adapted to grasp a distal tip coil on the guide wire. In another particular embodiment, a pair of spring-loaded tabs are used to grasp the distal tip coil of the guide wire to lock the filter assembly at the distal end of the guide wire. In this regard, the spring-loaded tabs are designed to latch onto the coils of the guide wire. The connector also may include three or more spring-loaded tabs designed to grasp and lock onto the guide wire tip coil.

In use, the present invention is able to capture embolic debris or other particulates entrained in the fluid of a blood vessel of a patient during, for example, an interventional procedure such as an angioplasty procedure or stenting procedure. Initially, a guide wire having a distal tip coil would be inserted into the body vessel and steered into the target area. Once the guide wire is delivered across the area of treatment, the filter assembly, which has a guide wire connector disposed at its distal end, would be delivered along the guide wire until it reaches the distal end of the guide wire. The guide wire connector would then be secured to the helical coil of the guide wire. The type of connection made at the distal coil tip will depend on the type of guide wire connector associated with the filter assembly. In order to transfer the filter assembly along the guide wire, the expandable basket of the filter assembly is maintained in a collapsed position by a delivery sheath which extends co-axially over the filter assembly. Alternatively, a rapid exchange delivery sheath could be used in which an offset lumen is utilized to maintain the filter assembly in a collapsed position. The delivery sheath, along with the collapsed filter assembly, can be delivered over the guide wire until the guide wire connector of the filter assembly locks the filter assembly to the guide wire. The filter assembly can be placed in its expanded position simply by retracting the delivery sheath proximally, allowing the expandable basket to self deploy. As the struts of the basket expand radially, so does the filter element which will now be deployed within the body vessel to collect embolic debris and particles that may be released into the bloodstream as the physician performs the interventional procedure. The delivery sheath can be removed from the guide wire to allow an interventional device to be delivered over the guide wire to the area of treatment. After the procedure is completed, the interventional device is removed from the guide wire and a recovery sheath can be delivered along the guide wire and over the filter assembly to return it to its collapsed position. The guide wire, along with the sheath and filter assembly, can be then removed from the patient.

When an overlapping connection coil is utilized, the delivery sheath may be rotated in order to interconnect the connecting coil onto the helical coil of the guide wire. It is contemplated that the guide wire could be rotated itself or simultaneously rotated with the delivery sheath to screw the connecting coil onto the tip coil of the guide wire. In another embodiment in which the connector includes spring-loaded tabs, the delivery sheath can be moved in a distal direction forcing the spring-loaded tabs to grasp one of the coils of the guide wire. It is contemplated that once the sheath delivers the filter assembly to the distal end of the guide wire, the guide wire could be moved in a proximal direction while holding the delivery sheath steady to force the spring-loaded tabs into a recess formed between adjacent coils.

In an alternative embodiment, the distal tip coil of the guide wire may include a rotating portion mounted onto the guide wire and used for attachment to the filter assembly. In this manner, once the guide wire connector is attached to the rotating coil section of the guide wire, the filter assembly will be free to spin or rotate relative to the guide wire. The filter assembly will remain stationary in a deployed position within the patient even if the guide wire is rotated by the user. In another particular embodiment, the guide wire includes a rotating coil section rotatably mounted on the guide wire. The rotating coil section can be placed between a pair of stationary coil sections which cooperate to form a composite tip coil.

It is to be understood that the present invention is not limited by the embodiments described herein. Alternatively, the present invention can be used in arteries, veins, and other body vessels. By altering the size of this design, it also may be suitable for peripheral and neurological applications. Other features and advantages of the present invention will become more apparent from the following detailed description of the invention, when taken in conjunction with the accompanying exemplary drawings.

DETAILED DESCRIPTION OF THE PREFERRED EMBODIMENTS

Figure 1:
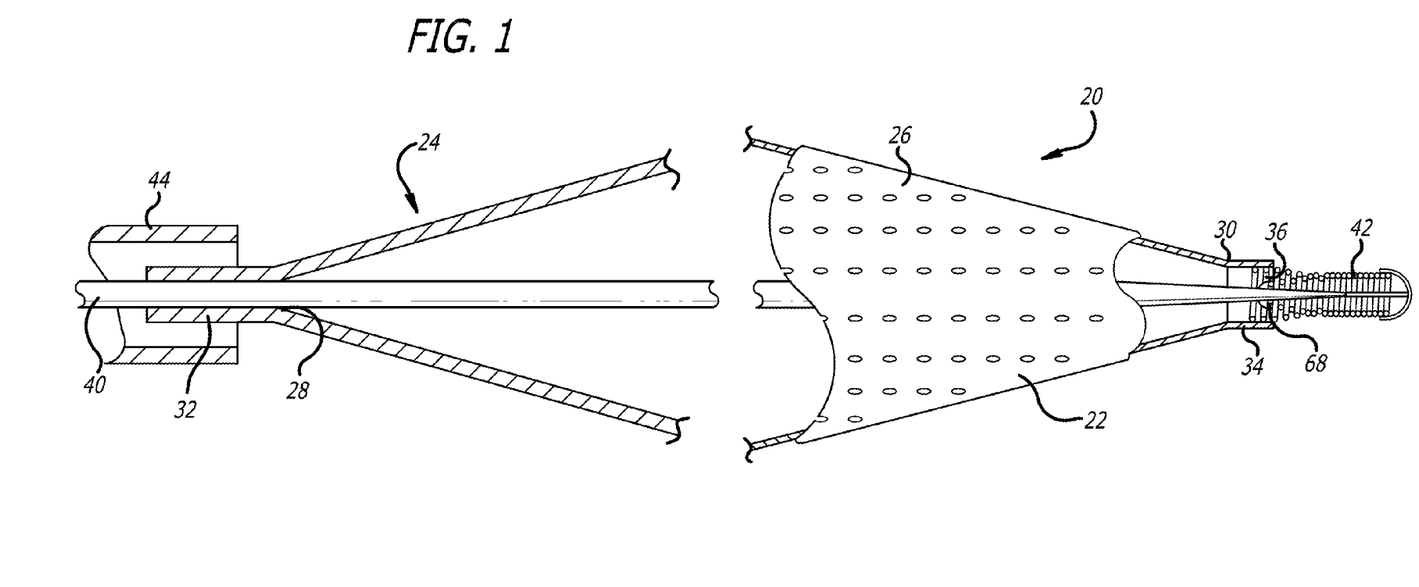
FIG. 1 is an elevational view, partially in cross-section and partially fragmented, of a guide wire with an embolic filter assembly embodying features of the present invention.

Turning now to the drawings, in which like reference numerals represent like or corresponding elements in the drawings, FIG. 1 illustrates one particular embodiment of an embolic filtering device 20 incorporating features of the present invention. This embolic filtering device 20 is designed to capture, for example, embolic debris which may be created and released into a body vessel during an interventional procedure. The embolic filtering device also can be used to filter any unwanted particles entrained in the fluid of a body vessel, such as large microspheres of a therapeutic agent which may be released into the vessel during a localized drug delivery procedure.

The embolic filtering device 20 includes an expandable filter assembly 22 having a self-expanding basket or cage 24 and a filter element 26 attached thereto. The filter assembly 22 has a proximal or first end 28 and a distal or second end 30, and in the embodiment shown in FIG. 1, there is a first sleeve or collar 32 disposed on the first end and a second sleeve or collar 34 disposed on the second end. The first and second sleeves 32 and 34 can be both cylindrically shaped. A guide wire connector 36 can be attached to the second end 30 of the filter assembly 22, and as shown in FIG. 1, the guide wire connector is directly attached to the distal or second sleeve 34. In this figure, the expandable filter assembly 22 is engaged with an elongated (solid or hollow) cylindrical tubular shaft, such as a steerable guide wire 40 having a distal tip coil 42. The guide wire 40 has a proximal end (not shown in FIG. 1) which extends outside the patient and is delivered by the physician across a target area in the patient's vasculature. A restraining or delivery sheath 44 delivers the filter assembly 22 separately along the guide wire 40 in order to maintain the expandable filter assembly 22 in its collapsed position until it is ready to be deployed within the patient's vasculature. In the particular embodiment shown in FIG. 1, the physician may rotate the delivery sheath 44 to attach the guide wire connector 36 to the helical tip coil 42 of the guide wire 40. Then, once connected to the guide wire 40, the expandable filter assembly 22 can be deployed by the physician by simple retracting the delivery sheath 44 proximally to expose the expandable filter assembly. Once the restraining sheath is retracted, the self-expanding basket 24 immediately begins to expand within the body vessel, causing the filter element 26 to expand as well.

Figure 2:
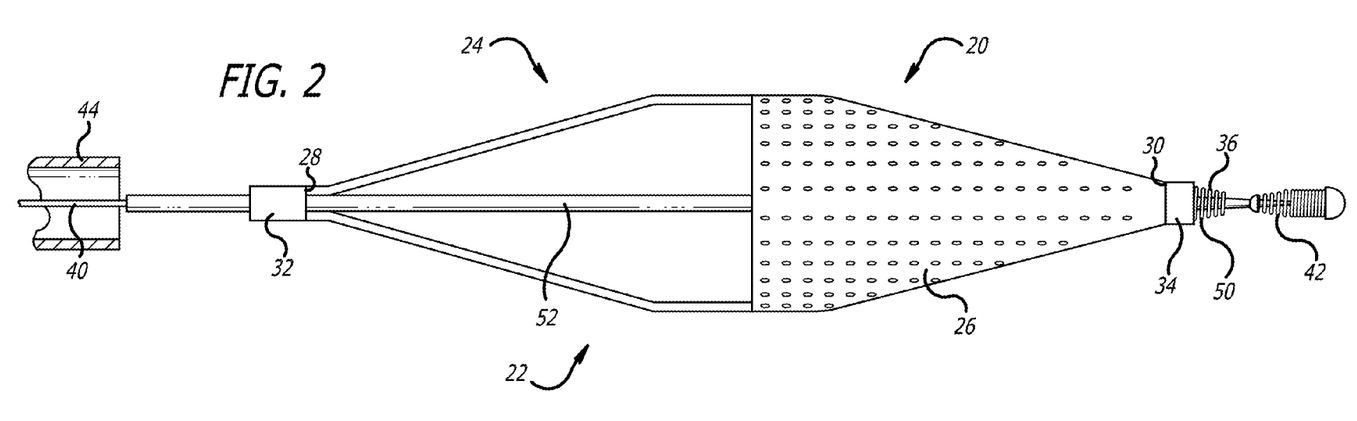
FIG. 2 is an elevational view of one embodiment of a filter assembly, similar to the one shown in FIG. 1, having a connection coil disposed on a distal end.

One embodiment of the embolic filtering device is shown in FIG. 2 in which the guide wire connector is a connection coil 50 disposed on the second sleeve 34. The connection coil 50 is able to be screwed onto the helical tip coil 42 of the guide wire 40. In the embodiment of FIG. 2, the expandable filter assembly 22 includes a tubular member or shaft 52 connected to the first and second ends 28 and 30 and is slidably disposed upon the guide wire 40. One of these first or second ends 28 should include a slip connection to allow the basket to elongate when it collapses and shorten when it expands. Alternatively, tubular member 52 could be fixed at both ends 28 and 30 and be made from a coil that can lengthen and shorten as needed. This same structure can be applied to any of the other embodiments described herein. This shaft 52 helps to maintain the integrity of the filter assembly as the filter assembly is being retracted by a recovery sheath. The filter assembly 22 and delivery sheath 44 are separately rotatable on the guide wire 40 during delivery to the distal end of the guide wire. Even when the connection coil 50 is coupled to the helical coil 42 of the guide wire 40, the filter assembly 22 can be separately rotatable independent from the guide wire. This can be accomplished by having the filter assembly 22 rotate independently of the second sleeve 34, which would be joined to the guide wire 40 through the coil connector 50.

Figure 3:
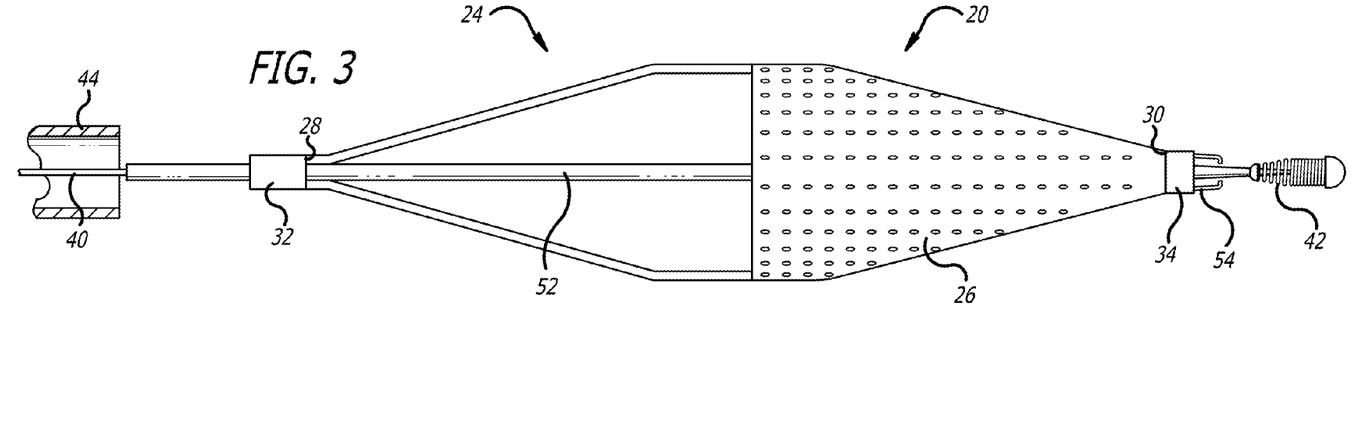
FIG. 3 is an elevational view of another embodiment of a filter assembly having a pair of spring-loaded tabs disposed on the distal end.

Referring now to FIG. 3, another embodiment is shown where the connector 36 is a spring-loaded tab 54, and more specifically a pair of spring-loaded tabs 54 disposed opposite one another on the second sleeve 34. In operation, the spring-loaded tabs on the distal end 30 of the filter assembly 22 would catch one of the coils of the tip coil 42 of the guide wire 40. It is also contemplated that there could be one or more spring-loaded tabs disposed on the second sleeve 34 that would catch the coil of the guide wire 40. One advantage of using spring-loaded tabs 54 is that the guide wire connector does not have to be rotated to be attached to the tip coil of the guide wire.

Figure 4:
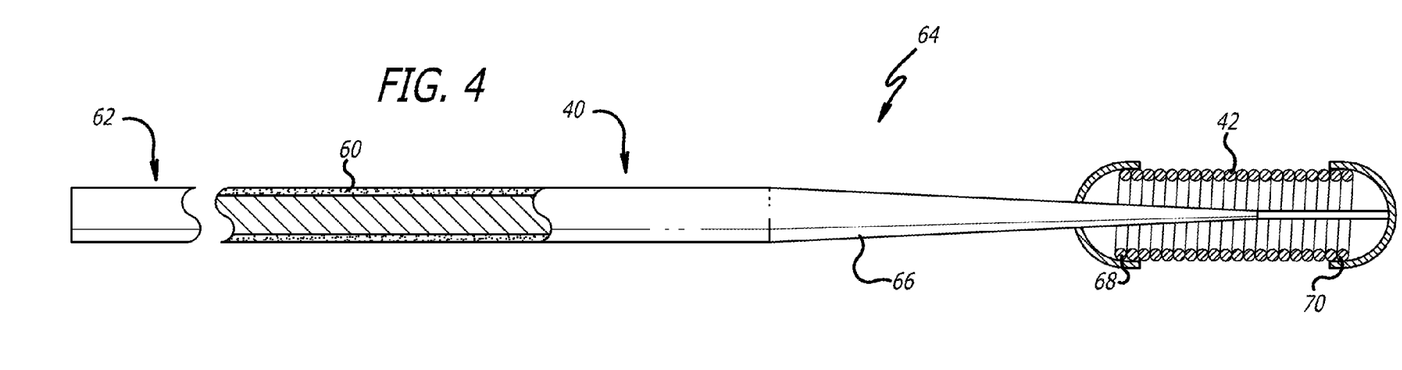
FIG. 4 is an elevational view, partially in cross section, of a conventional guide wire including a helical coil.

The embolic filtering device 20 can be constructed with a conventional guide wire 40 having a tip coil 42 disposed at a distal end. Referring now to FIG. 4, a conventional guide wire 40 is shown. The guide wire 40 depicted in FIG. 4 has an elongate core member 60 with a proximal section 62 and a distal section 64. This embodiment shows the distal section 64 of the guide wire 40 having at least one distally tapered portion 66. A flexible body member or helical coil 42 is disposed around the distal section 64, and the helical coil has a proximal end 68 and a distal end 70. In this embodiment the helical coil 42 has a relatively constant diameter from the proximal end 68 to the distal end 70. The helical coil 42 is attached to the guide wire 40 at both the proximal end 68 and the distal end 70. In the event that the spacing between coils is too tight, i.e., the tip is too stiff and will not bend through tortuous anatomy, the physician can simply apply a small amount of proximal force to portion 68 to cause a portion of the tip coil to expand longitudinally, thus creating space between coils which enhance the ability of the spring-like tabs to catch and hold onto the tip coil.

Figure 5:
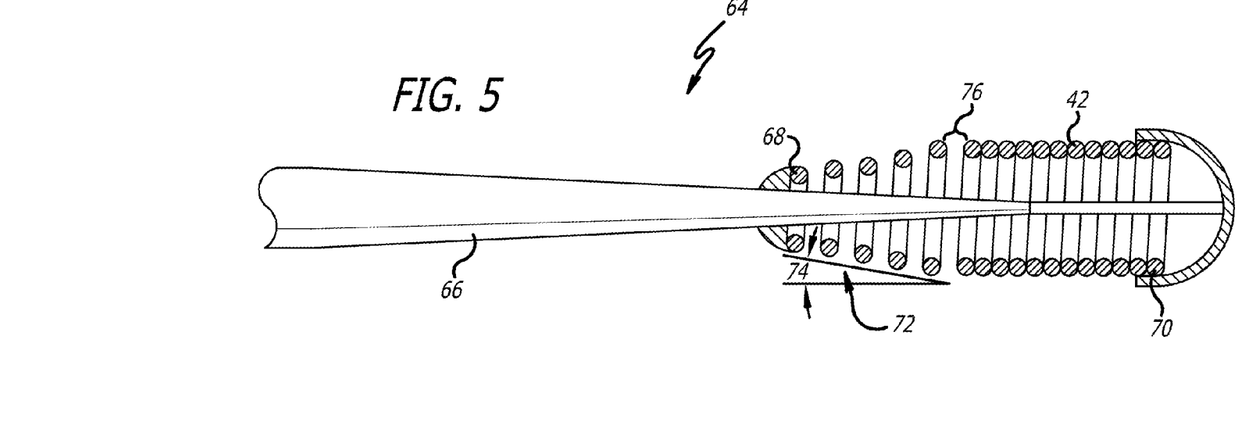
FIG. 5 is an enlarged view of a distal portion of a guide wire having a proximally tapered stretched helical coil.

In another embodiment however, the helical coil 42 has a tapered proximal end 72, shown in FIG. 5, which is similar to the proximally tapered coil found in U.S. Pat. No. 6,132,389 issued to Cornish et al. A tapered angle 74 of the tapered proximal end 72 is the angle the tangent to the tapered section 66 makes with the longitudinal axis of the helical coil 40, can be from about 0.1 to 10° and preferably about 0.5 to 2°. The distal end 70 of the helical coil 42 typically has an outer diameter approximately equal to the nominal outer diameter of the proximal section 62 of the elongate core member 60. Details of a guide wire having a proximally tapered helical coil can be found in the Cornish et al. patent. The tapered proximal end 72 shown in FIG. 5 differs from the proximal tapered helical coil found in the Cornish et al. patent in that the tapered proximal end is somewhat stretched, forming spaces or gaps 76 in between individual coils. This embodiment allows the connection coil to screw onto the stretched proximal tapered helical coil and lock in place within the gaps 76. When using a proximally tapered helical coil and a connection coil 50 on the filter assembly 22, it may be preferred that both have a similar pitch. The increased gap between adjacent coils again helps to enhance the ability of the spring-loaded tabs to latch onto a coil(s).

Figure 6:
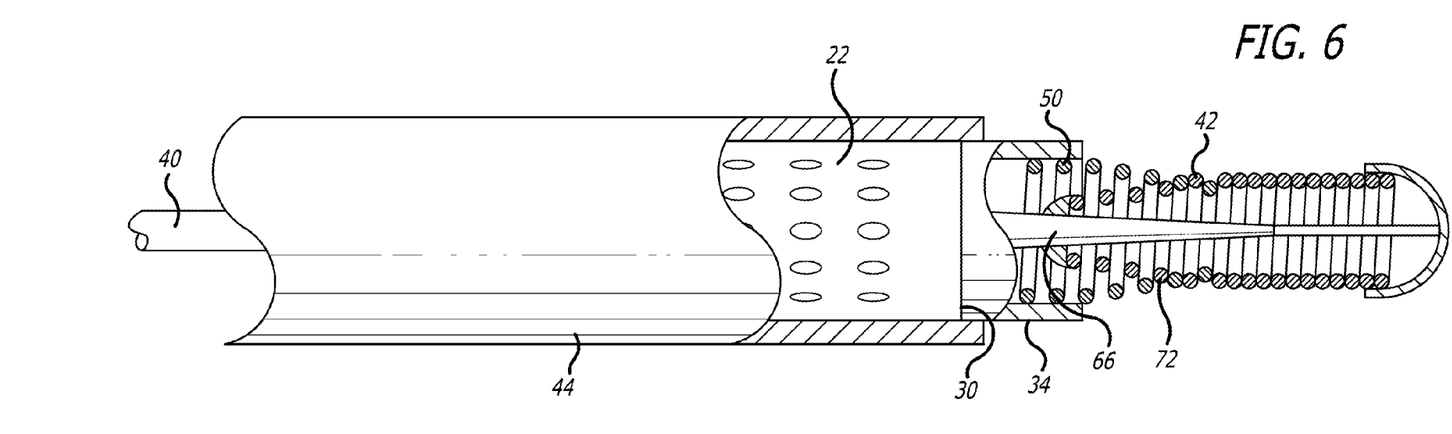
FIG. 6 is an elevational view, partially in cross-section of one embodiment of a filter assembly in a collapsed position and including a connection coil attached to the helical coil of a guide wire.

Referring now to FIG. 6, the embodiment of the present invention which uses a connection coil 50 disposed on the second sleeve 34 to lock the filter assembly into place is shown in greater detail. This figure also shows the filter assembly 22 being held in a collapsed position inside the delivery sheath 44. In order to connect the filter assembly 22 to the helical coil 42 of the guide wire 40, the delivery sheath is rotated clockwise, screwing the connection coil 50 onto the helical coil 42. It is also contemplated that the guide wire could be rotated counter-clockwise or rotated simultaneously with the sheath to screw the connection coil 50 onto the helical coil 42. Once the filter assembly 22 is secured onto the guide wire 40, the delivery sheath 44 can then be withdrawn, allowing the filter assembly to expand.

Figure 7A:
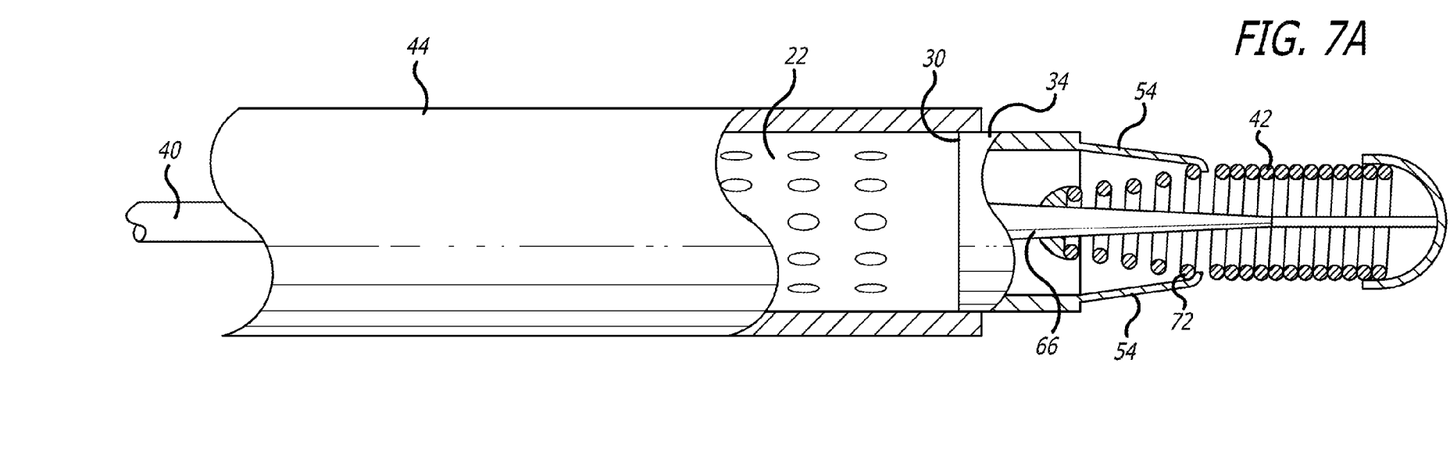
FIG. 7A is an elevational view, partially in cross-section of one embodiment of a filter assembly in a collapsed position and including spring-loaded tabs attached to the helical coil of a guide wire.

Now referring to FIG. 7A, the present invention is shown in which the filter assembly 22 includes spring-loaded tabs 54 disposed on the second sleeve 34 and locked into place on the tapered proximal end 72 of the helical coil 42. The spring-loaded tabs 54 are caught inside the helical coil 42, however, the spring-loaded tabs may be designed to grab around the outside of the helical coil. In order to hook the spring-loaded tabs 54 into or around the helical coil 42, the delivery sheath 44 may have to be forced or pushed proximally into the helical coil of the guide wire. It is also contemplated that the guide wire 40 may be forced or pulled distally into the spring-loaded tabs 54 to hook the spring-loaded tabs onto the helical coil. As with the embodiment shown in FIG. 6, once the spring-loaded tabs 54 are secured to the guide wire 40, the delivery sheath 44 may then be withdrawn so the filter assembly may expand.

Figure 7B:
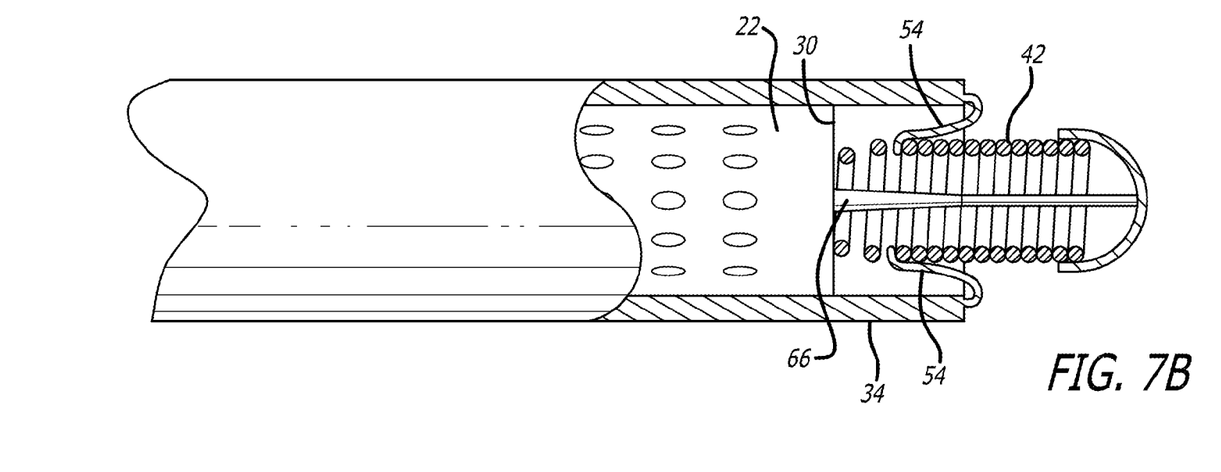
FIG. 7B is an elevational view, partially in cross-section of another embodiment of a filter assembly including spring-loaded tabs which extend proximally for attachment to the helical coil of a guide wire.
Figure 7C:
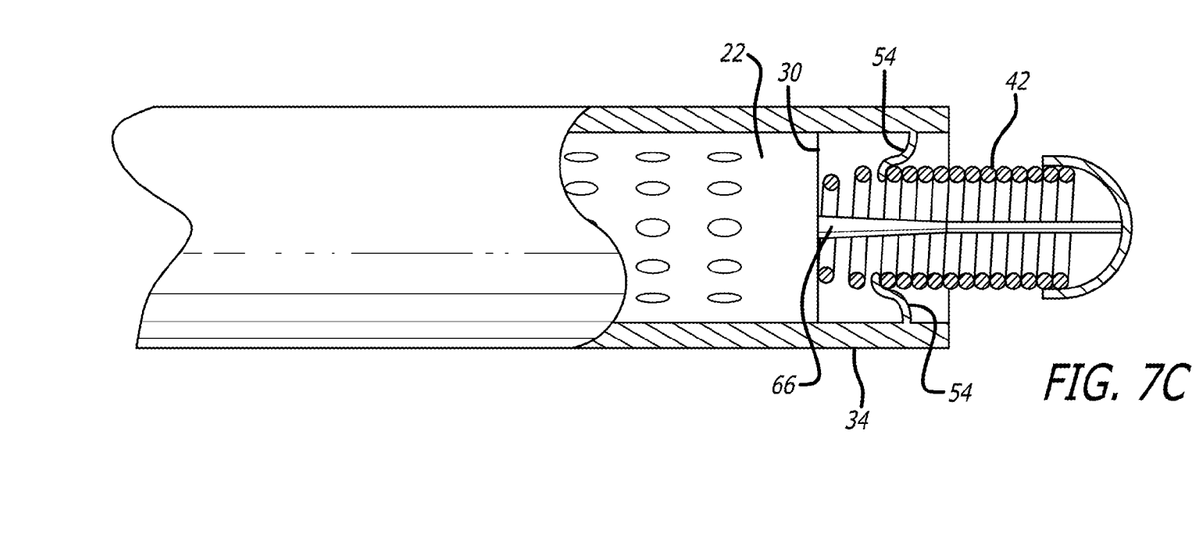
FIG. 7C is an elevational view, partially in cross-section of another embodiment of a filter assembly including spring-loaded tabs which extend proximally for attachment to the helical coil of a guide wire.

An alternative embodiment of the filter assembly of FIG. 7A is shown in FIG. 7B. In this particular embodiment, the filter assembly includes spring-loaded tabs 54 disposed on the second sleeve 34 which extend proximally rather than distally, as is shown in FIG. 7A. In this particular embodiment, the spring-loaded tabs 54 will lock into place on the helical coil 42. This particular embodiment may help to ease the insertion of the tabs 54 into the helical coil 42 and also may enhance the holding power of this connection. Another alternative design is shown in FIG. 7C in which the spring-loaded tabs 54 are again disposed to extend proximally from the second sleeve 34. Both of the embodiments shown in FIGS. 7B and 7C have spring-loaded tabs facing proximally which will tend to wedge tighter once the filter assembly 22 comes in contact with the helical coil 42. Additionally, these particular embodiments may help to hold the filter assembly 22 tighter onto the guide wire via the helical coil 42 in the event that the filter assembly 22 is ever caught in the patient's anatomy and the guide wire is pulled proximally.

Figure 8:
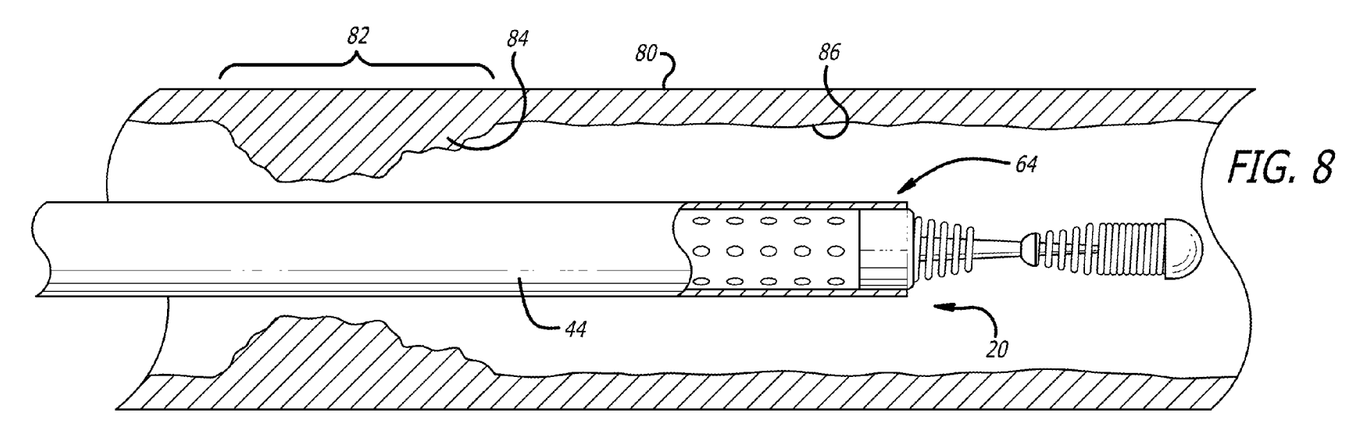
FIG. 8 is an elevational view, partially in cross-section, of a filter assembly in a collapsed position attached to the helical coil of a guide wire, within a body vessel at a downstream location from an area to be treated.
Figure 9:
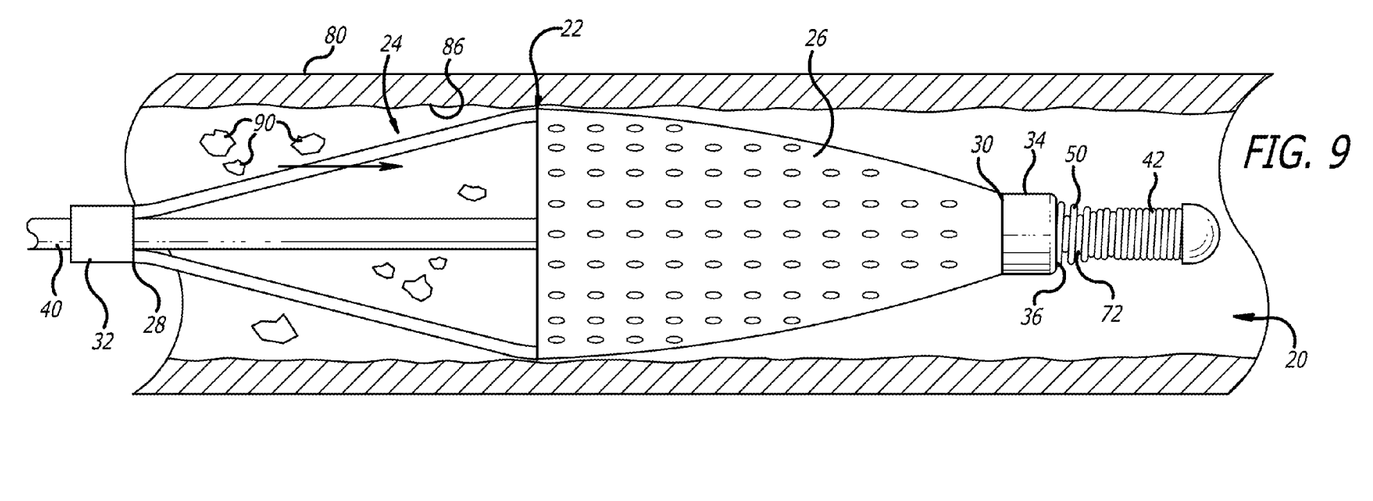
FIG. 9 is an elevational view, partially in cross-section, similar to that shown in FIG. 8, wherein the filter assembly is deployed in its expanded position within the body vessel for filtering purposes.

In FIGS. 8 and 9, the embolic filtering device 20 is shown within an artery 80 or other body vessel of the patient. This portion of the artery 80 has an area of treatment 82 in which, for example, atherosclerotic plaque 84 has built up against the inside wall 86 of the artery 80. In operation, the physician would first insert the guide wire 40 into the vasculature of the patient, positioning the distal section 64 of the guide wire across the area of treatment 82 with the distal end and helical coil 42 located downstream from the area of treatment. Next, the delivery sheath 44 delivers the filter assembly 22 separately along the guide wire 40 in order to maintain the expandable filter assembly 22 in its collapsed position. The physician manipulates the sheath 44 and/or the guide wire 40 to join the connector 36, in this embodiment the connection coil 50, to the helical coil 42. Once the filter assembly 22 is joined to the helical coil 42, the expandable filter assembly 22 is expanded by the physician by simply retracting the delivery sheath 44 proximally to expose the expandable filter assembly. Once the restraining sheath is retracted, the self-expanding cage 24 immediately begins to expand within the body vessel, causing the filter element 26 to expand as well. By attaching the filter assembly 22 to the guide wire after the guide wire has been delivered to the area of treatment 82, the physician is able to deliver the guide wire with "front-line" capabilities and is still able to obtain embolic protection as a separate attachment.

Referring now to FIG. 9, the embolic filtering device 20 is shown in its expanded position within the patient's artery 80. Any embolic debris 90 created during an interventional procedure will be released into the bloodstream and will enter the filter assembly 22 located downstream from the area of treatment 82. Once the procedure is completed and the embolic debris 90 is collected in the filter element 26, the filter assembly 22 can be collapsed by a recovery sheath 44 which slides over the filter assembly, allowing the embolic filter device 20 to be removed from the patient's vasculature.

When the filtering assembly 22 is collapsed by the recovery sheath, there is a possibility that the proximal end of the filter assembly may move somewhat distally as the end of the recovery sheath contacts the assembly. This may occur, for example, in the embodiment shown in FIG. 1, since the proximal end of the filter assembly is not physically attached to the guide wire, but rather is slidably disposed on the guide wire. This may not occur if the expandable basket has sufficient axial stiffness. However, when a filter assembly such as the one in FIG. 1 is utilized, a recovery sheath having a large inner diameter may be used to capture a greater portion of the proximal end of the filter assembly. As a result, the recovery sheath may help to prevent the proximal end from moving distally as the sheath slides over the filter assembly. Another way to prevent the end from moving is to utilize a tubular member or shaft, such as is shown in the embodiments of FIGS. 2 and 3. The tubular shaft 52 provides axial rigidity which prevents the proximal end of the filter assembly from being pushed distally as a recovery sheath extends over the filter assembly. Again, the distal connection of the tubular shaft 52 and basket should be a sliding fit in order to allow the basket to open and close. The tubular shaft 52 used in accordance with the embodiments of FIGS. 2 and 3 is just one example of adding stiffness in a longitudinal direction to enhance the ability of the filter assembly to be collapsed by the recovery sheath.

Figures 10A, 10B, 11, 12:
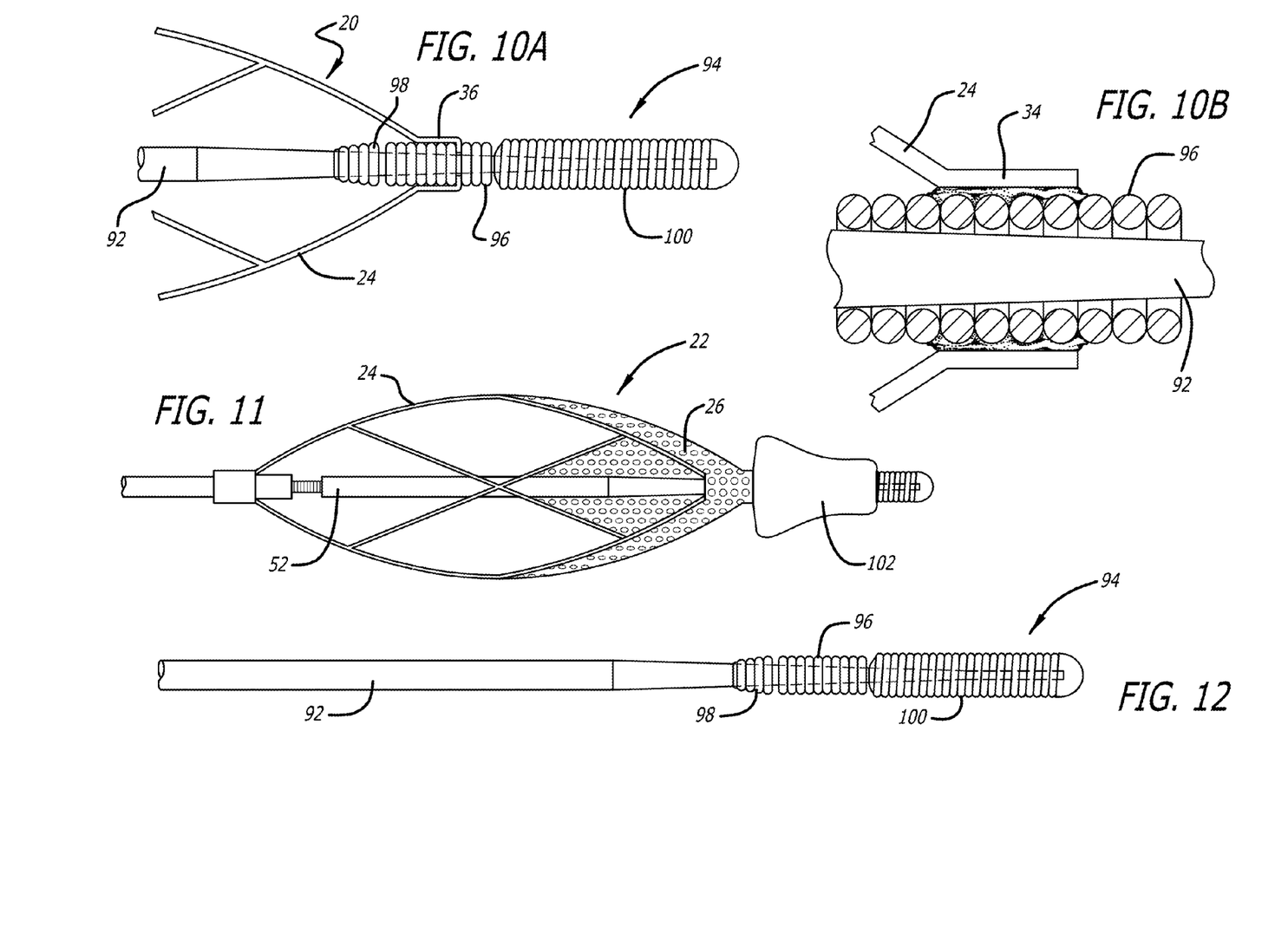
FIG. 10A is an elevational view, partially in cross-section, of the end an expandable basket of a filter assembly (shown without the filter member) in a deployed position and attached to a rotating coil section forming a portion of the distal tip coil of a guide wire.
FIG. 10B is an elevational view of the distal end of filter assembly which can be permanently mounted to the rotating coil section forming a portion of the distal tip coil of a guide wire.
FIG. 11 is an elevational view of one particular embodiment of a filter assembly, similar to the one shown in FIG. 10, which can be used in accordance with the present invention.
FIG. 12 is an elevational view of a distal portion of a guide wire having a rotating coil section.

Referring now to FIGS. 10-12, another embodiment of the embolic filtering device 20 is shown as it is rotatably mounted onto the specially adapted guide wire 92. In this particular embodiment, the guide wire 92 has a composite tip coil 94 including a rotating coil section 96 which is rotatably mounted to the core of the guide wire 92. This rotating coil section is disposed between a proximal coil section 98 and a distal coil section 100 which are both fixed to the core of the guide wire. The proximal coil section 98 and the distal coil section 100 act as stop fittings to maintain the rotating coil segment 96 longitudinally fixed there between, yet allows the rotating coil segment to rotate relative to the guide wire. The proximal coil section 98 and distal coil section 100, along with the rotating coil section 96, cooperatively form a composite tip coil which can be bent to a J-shaped configuration, or other configuration, as is well-known in the art, to aid in the steering of the guide wire through the patient's anatomy.

The guide wire connector 36 is adapted to engage and attach to the rotating coil section 96 which forms the composite tip coil 94. The guide wire connector 36 which can be used in accordance with this embodiment can be either the connection coil described above or the spring-loaded tabs described in conjunction with the embodiment of FIG. 3.

As can be better seen in FIG. 12, the rotating coil section 96 is disposed between the proximal coil section 98 and the distal coil section 100. It should be appreciated that the outer diameter of the proximal coil section 98 may be somewhat smaller than the outer diameter of the rotating coil section 96 to allow the distal end of the filter assembly to extend thereover when the connection to the rotating coil section is being performed. When the spring-loaded tabs are utilized, the gaps between the coils of the rotating coil section 96 may be increased to provide gaps which help the tabs to latch onto the coils of the rotating coil section.

As can be seen in FIG. 11, the filter assembly 22 may include an obturator 102 made from a soft material such as PEBAX 40D which provides an atraumatic tip to the filter assembly as it is being advanced over the guide wire within the patient's vasculature. The soft-tipped obturator 102 helps to prevent the distal end of the filter from scraping the walls of the body vessel as it is being advanced therethrough. This same type of obturator can be used to in accordance with any of the other embodiments of the filter assembly used in accordance with the present invention.

Alternatively, as in shown in FIG. 10B, the distal end of the filter assembly 22 can be soldered directly to the rotating coil section 96 to create a one-piece embolic filtering device which can also be used during the performance of interventional procedures for capturing any embolic debris which may be created. If the distal end of the filter assembly is permanently attached to the rotating coil section 96, then the filtering assembly would not be able to be delivered separately once the guide wire has been steered into the target area in the patient's vasculature, but rather, would move with the distal end of guide wire along with the delivery sheath which maintains it in its collapsed position. Such a composite filter/guide wire could be delivered into a patient's vasculature for particulate filtration.

The guide wire connector 36 made in accordance with the present invention has been shown as it is connected to the distal sleeve which forms part of the expandable basket of the filter assembly. However, the guide wire connector also could be formed on the tubular shaft 52 used in accordance with the embodiments of the filter assemblies of FIGS. 2 and 3. It also can be a separate piece which is bonded or otherwise attached to the distal end of any conventional filtering assembly. Accordingly, the guide wire connector 36 can take on many different shapes and forms other than those shown in the particular figures disclosed herein to perform the same function as that disclosed herein. It should be appreciated that modifications can be made to the guide wire, filter assembly and guide wire connector without departing from the spirit and scope of the present invention.

It should be appreciated that the guide wire connectors could be placed on the proximal end of the filter assembly, rather than the distal end. The guide wire connectors are shown attached to the distal most end of the filter assemblies in the particular embodiments described herein. However, similar type connectors could be placed on the proximal end of the filter assembly without departing from the spirit and scope of the present invention.

The expandable basket of the present invention can be made in many ways. One particular method of making the basket is to cut a thin-walled tubular member, such as nickel-titanium hypotube, to remove portions of the tubing in the desired pattern for each strut, leaving relatively untouched the portions of the tubing which form the structure. The tubing may be cut into the desired pattern by means of a machine-controlled laser. The tubing used to make the basket could possibly be made of suitable biocompatible material, such as spring steel. Elgiloy is another material which could possibly be used to manufacture the basket. Also, very elastic polymers possibly could be used to manufacture the basket.

The strut size is often very small, so the tubing from which the basket is made may have a small diameter. Typically, the tubing has an outer diameter on the order of about 0.020-0.040 inches in the unexpanded condition. Also, the basket can be cut from large diameter tubing. Fittings are attached to both ends of the lased tube to form the final basket geometry. The wall thickness of the tubing is usually about 0.076 mm (0.001-0.010 inches). As can be appreciated, the strut width and/or depth at the bending points will be less. For baskets deployed in body lumens, such as PTA applications, the dimensions of the tubing may be correspondingly larger. While it is preferred that the basket be made from laser cut tubing, those skilled in the art will realize that the basket can be laser cut from a flat sheet and then rolled up in a cylindrical configuration with the longitudinal edges welded to form a cylindrical member.

Generally, the tubing is put in a rotatable collet fixture of a machine-controlled apparatus for positioning the tubing relative to a laser. According to machine-encoded instructions, the tubing is then rotated and moved longitudinally relative to the laser which is also machine-controlled. The laser selectively removes the material from the tubing by ablation and a pattern is cut into the tube. The tube is therefore cut into the discrete pattern of the finished struts. The basket can be laser cut much like a stent is laser cut. Details on how the tubing can be cut by a laser are found in U.S. Pat. Nos. 5,759,192 (Saunders), 5,780,807 (Saunders) and 6,131,266 (Saunders) which have been assigned to Advanced Cardiovascular Systems, Inc.

The process of cutting a pattern for the strut assembly into the tubing generally is automated except for loading and unloading the length of tubing. For example, a pattern can be cut in tubing using a CNC-opposing collet fixture for axial rotation of the length of tubing, in conjunction with CNC X/Y table to move the length of tubing axially relative to a machine-controlled laser as described. The entire space between collets can be patterned using the $CO_2$ or Nd:YAG laser set-up. The program for control of the apparatus is dependent on the particular configuration used and the pattern to be ablated in the coding.

A suitable composition of nickel-titanium which can be used to manufacture the strut assembly of the present invention is approximately 55% nickel and 45% titanium (by weight) with trace amounts of other elements making up about 0.5% of the composition. The austenite transformation temperature is between about 0° C. and 20° C. in order to achieve superelasticity at human body temperature. The austenite temperature is measured by the bend and free recovery tangent method. The upper plateau strength is about a minimum of 60,000 psi with an ultimate tensile strength of a minimum of about 155,000 psi. The permanent set (after applying 8% strain and unloading), is less than approximately 0.5%. The breaking elongation is a minimum of 10%. It should be appreciated that other compositions of nickel-titanium can be utilized, as can other self-expanding alloys, to obtain the same features of a self-expanding basket made in accordance with the present invention.

In one example, the basket of the present invention can be laser cut from a tube of nickel-titanium (Nitinol) whose transformation temperature is below body temperature. After the strut pattern is cut into the hypotube, the tubing is expanded and heat treated to be stable at the desired final diameter. The heat treatment also controls the transformation temperature of the basket such that it is super elastic at body temperature. The transformation temperature is at or below body temperature so that the basket is superelastic at body temperature. The basket is usually implanted into the target vessel which is smaller than the diameter of the basket in the expanded position so that the struts of the basket apply a force to the vessel wall to maintain the basket in its expanded position. It should be appreciated that the basket can be made from either superelastic, stress-induced martensite NiTi or shape-memory NiTi.

The basket could also be manufactured by laser cutting a large diameter tubing of nickel-titanium which would create the basket in its expanded position. Thereafter, the formed basket could be placed in its unexpanded position by back-loading the basket into a restraining sheath which will keep the device in the unexpanded position until it is ready for use. If the basket is formed in this manner, there would be no need to heat treat the tubing to achieve the final desired diameter. This process of forming the basket could be implemented when using superelastic or linear-elastic nickel-titanium.

The struts forming the proximal struts can be made from the same or a different material than the distal struts. In this manner, more or less flexibility for the proximal struts can be obtained. When a different material is utilized for the struts of the proximal struts, the distal struts can be manufactured through the lazing process described above with the proximal struts being formed separately and attached. Suitable fastening means such as adhesive bonding, brazing, soldering, welding and the like can be utilized in order to connect the struts to the distal assembly. Suitable materials for the struts include superelastic materials, such as nickel-titanium, spring steel, Elgiloy, along with polymeric materials which are sufficiently flexible and bendable.

The polymeric material which can be utilized to create the filtering element include, but is not limited to, polyurethane and Gortex, a commercially available material. Other possible suitable materials include ePTFE. The material can be elastic or non-elastic. The wall thickness of the filtering element can be about 0.00050-0.0050 inches. The wall thickness may vary depending on the particular material selected. The material can be made into a cone or similarly sized shape utilizing blow-mold technology or dip molding technology. The openings can be any different shape or size. A laser, a heated rod or other process can be utilized to create to perfusion openings in the filter material. The holes, would of course be properly sized to catch the particular size of embolic debris of interest. Holes can be lazed in a spinal pattern with some similar pattern which will aid in the re-wrapping of the media during closure of the device. Additionally, the filter material can have a "set" put in it much like the "set" used in dilatation balloons to make the filter element re-wrap more easily when placed in the collapsed position.

The materials which can be utilized for the restraining sheath can be made from polymeric material such as cross-linked HDPE. This sheath can alternatively be made from a material such as polyolifin which has sufficient strength to hold the compressed strut assembly and has relatively low frictional characteristics to minimize any friction between the filter assembly and the sheath. Friction can be further reduced by applying a coat of silicone lubricant, such as Microglide®, to the inside surface of the restraining sheath before the sheath is placed over the filter assembly. Silicone also can be placed on the filter material as well.

Further modifications and improvements may additionally be made to the device and method disclosed herein without departing from the scope of the present invention. Accordingly, it is not intended that the invention be limited, except as by the appended claims.

What is claimed is:

1. An apparatus for embolic protection, comprising:
    a guide wire having a proximal end portion and a tip coil disposed on a distal end, said tip coil having a rotating coil section rotatably mounted on the guide wire to allow free relative rotation between the guide wire and the rotating coil section; and
    a filter assembly disposed for traveling along the guide wire from a first configuration at the proximal end portion to a second configuration at the distal end, the filter assembly including a first end and a second end, and a guide wire connector disposed on one of the ends of the filter assembly, said guide wire connector coupled to said rotating coil section in the second configuration and said guide wire connector uncoupled to said rotating coil in the first configuration.

2. The apparatus of claim 1, wherein the guide wire connector includes a connection coil.

3. The apparatus of claim 1, wherein the guide wire connector includes a spring-loaded tab.

4. The apparatus of claim 1, wherein the filter assembly includes a plurality of self-expanding struts disposed between the first and second ends.

5. The apparatus of claim 1, wherein the guide wire connector is attached to the first end of the filter assembly.

6. The apparatus of claim 1, wherein the guide wire connector is attached to the second end of the filter assembly.

7. The apparatus of claim 1, wherein the guide wire connector includes a pair of oppositely disposed, spring-loaded tabs adapted to engage the rotating coil section.

8. The apparatus of claim 1, wherein the rotating coil section of the guide wire includes gaps formed therein to create openings for receiving the guide wire connector.

9. The apparatus of claim 8, wherein the guide wire connector includes a projection adapted to extend within a gap formed on the rotating coil section.

10. An apparatus for embolic protection, comprising:
    a guide wire having a tip coil disposed on a distal end, said tip coil having a rotating coil section rotatably mounted on the guide wire to allow free relative rotation between the guide wire and the rotating coil section; and
    a filter assembly disposed for traveling along the guide wire, the filter assembly including a first end and a second end, and a guide wire connector disposed on one of the ends of the filter assembly, said guide wire connector coupled to said rotating coil section, wherein the rotating coil section of the coil tip is disposed between a proximal coil section fixed to the guide wire and a distal coil section fixed to the guide wire.

11. The apparatus of claim 10, wherein the rotating coil section of the coil tip has an outer diameter which is greater than the outer diameter of the proximal coil section.

12. An apparatus for embolic protection, comprising:
    a guide wire having a tip coil disposed on a distal end, said tip coil having a rotating coil section rotatably mounted on the guide wire wherein the rotating coil section of the coil tip is disposed between a proximal coil section and a distal coil section which are fixed to the guide wire to restrict longitudinal movement of the rotating coil section with respect to the guide wire while allowing rotation of the rotating coil section relative to the guide wire; and
    a filter assembly including a proximal end and a distal end, one of said proximal and distal ends having a guide wire connector disposed thereon, the guide wire connector being coupled to the rotating coil section.

13. The apparatus of claim 12, wherein the distal end of the filter assembly is coupled to the rotating coil section of the tip coil.

14. The apparatus of claim 12, wherein the guide wire connector includes a pair of oppositely disposed, spring-loaded tabs adapted to engage the rotating coil section.

15. The apparatus of claim 12, wherein the rotating coil section of the guide wire includes gaps formed therein to create openings for receiving the guide wire connector.

16. The apparatus of claim 15, wherein the guide wire connector includes a projection adapted to extend within a gap formed on the rotating coil section.

17. An apparatus for embolic protection, comprising:
    a guide wire having a rotating section rotatable mounted on the guide wire to restrict longitudinal movement of the rotating coil section with respect to the guide wire without preventing rotation of the rotating coil section relative to the guide wire; and a filter assembly including a proximal end and a distal end;
    wherein one end of the filter assembly has a guide wire connector disposed thereon, the guide wire connector is coupled to the rotating section of the guide wire, wherein the guide wire connector includes a pair of oppositely disposed, spring loaded tabs adapted to directly engage the rotating section.

18. The apparatus of claim 17, wherein the rotating section of the guide wire includes gaps formed therein to create openings for receiving the guide wire connector.

19. The apparatus of claim 18, wherein the guide wire connector includes projections adapted to extend with the gaps formed on the rotating section.

* * * * *